United States Patent
Chen et al.

(10) Patent No.: US 7,780,982 B2
(45) Date of Patent: Aug. 24, 2010

(54) BIODEGRADABLE HYALURONIC ACID DERIVATIVE AND BIODEGRADABLE POLYMERIC MICELLE COMPOSITION

(75) Inventors: Jui-Hsiang Chen, Hsinchu (TW);
Bin-Hong Tsai, Kaohsiung (TW);
Hsuen-Tseng Chang, Kaohsiung (TW);
Muh-Lan Chen, Hsinchu (TW);
Yu-Hua Chen, Taichung (TW);
Shu-Hua Jan, Changhua (TW);
Mei-Jung Liu, Miaoli (TW)

(73) Assignee: Industrial Technology Research Instittute, Chutung, Hsinchu (TW)

( * ) Notice: Subject to any disclaimer, the term of this patent is extended or adjusted under 35 U.S.C. 154(b) by 1261 days.

(21) Appl. No.: 10/992,387

(22) Filed: Nov. 18, 2004

(65) Prior Publication Data
US 2005/0123505 A1  Jun. 9, 2005

(30) Foreign Application Priority Data
Dec. 4, 2003  (GB) .................................. 0328168.0

(51) Int. Cl.
*A61K 9/127* (2006.01)
(52) U.S. Cl. ..................................................... 424/450
(58) Field of Classification Search .................. None
See application file for complete search history.

(56) References Cited

U.S. PATENT DOCUMENTS

| 4,851,521 | A |  | 7/1989 | della Valle et al. ......... 536/55.1 |
|---|---|---|---|---|
| 4,957,744 | A |  | 9/1990 | della Valle et al. .......... 424/401 |
| 5,122,598 | A |  | 6/1992 | della Valle et al. ............ 536/20 |
| 5,202,431 | A |  | 4/1993 | della Valle et al. ......... 536/55.1 |
| 5,336,767 | A |  | 8/1994 | della Valle et al. ......... 536/55.1 |
| 5,442,053 | A |  | 8/1995 | della Valle et al. ......... 536/55.1 |
| 5,462,976 | A |  | 10/1995 | Matsuda et al. ................ 522/74 |
| 5,510,418 | A | * | 4/1996 | Rhee et al. .................. 525/54.2 |
| 5,705,270 | A | * | 1/1998 | Soon-Shiong et al. ..... 428/402.2 |
| 5,856,299 | A |  | 1/1999 | Righetto et al. ................ 514/8 |
| 6,322,805 | B1 | * | 11/2001 | Kim et al. .................... 424/426 |
| 2005/0112172 | A1 | * | 5/2005 | Pacetti ......................... 424/423 |

FOREIGN PATENT DOCUMENTS

| GB | 2 151 244 A | 7/1985 |
|---|---|---|
| JP | 2001348401 | 12/2001 |
| SK | 46197 A | 3/1990 |
| WO | WO 99/43728 | 9/1999 |
| WO | WO 02/098923 A1 | 12/2002 |

OTHER PUBLICATIONS

European Patent Search Report.

* cited by examiner

*Primary Examiner*—Robert A Wax
*Assistant Examiner*—Melissa S Mercier
(74) *Attorney, Agent, or Firm*—Thomas, Kayden, Horstemeyer & Risley

(57) ABSTRACT

A biodegradable hyaluronic acid derivative comprising a modified hyaluronic acid repeating unit represented by the formula $(HA)-[O(C=O)NH-M]_p$, wherein HA is a unit including N-acetyl-D-glucosamine and D-glucuronic acid, M is a modifying moiety containing a $C_{2-16}$ hydrocarbyl group or a prepolymer, and p is an integer of 1 to 4. The biodegradable hyaluronic acid derivative when dissolved in a hydrophilic medium can form micelles and can be used to entrap a pharmaceutically active or bioactive molecule.

20 Claims, 15 Drawing Sheets

FIG. 9 C12-HA

FIG. 10 Mono functional PCL

FIG. 11 Mono-functional PLLA

HA-graft-PCL

HA-graft-PLLA

BIODEGRADABLE HYALURONIC ACID DERIVATIVE AND BIODEGRADABLE POLYMERIC MICELLE COMPOSITION

BACKGROUND OF THE INVENTION

1. Field of the Invention

The present invention relates to a biodegradable hyaluronic acid derivative, and more particularly to a biodegradable hyaluronic acid derivative resulting from the reaction of hydroxy groups in hyaluronic acid and isocyanate groups in an isocyanate group-containing compound via a urethane linkage.

2. Description of the Prior Art

Hyaluronan or hyaluronic acid is a linear mucopolysaccharide constituted by N-acetyl-D-glucosamine and D-glucuronic acid repeating units. Hyaluronic acid was first found in the vitreous body of the cattle eye by Meyer and Palmer in 1934, and then was found in other tissues such as extracellular matrix (ECM) and synovial fluid of the joints. Hyaluronic acid is a viscoelastic fluid filled in the space between cells and collagenous fibers and coated on some epidermal tissues. Hyaluronic acid plays an important role in the biological organism, firstly as a mechanical support of the cells of many tissues, such as the skin, the tendons, the muscles and cartilage. Hyaluronic acid also performs other functions in the biological processes, such as moistening of tissues, lubrication, and cellular migration.

Hyaluronic acid may be extracted from natural tissues, such as rooster's combs, or also from certain bacteria. The molecular weight of hyaluronic acid obtained by extraction varies due to the source and the extraction process and is generally in the range of several millions to several tens of millions Dalton.

Hyaluronic acid, its molecular fractions and its salts have been used in pharmaceutical, surgical and cosmetic fields and in the field of biodegradable polymer materials. However, since hyaluronic acid is very expensive and is biodegraded quite easily, its application is limited. In past years, many methods have been developed to modify hyaluronic acid in order to increase its resistance to biodegradation.

In U.S. Pat. No. 5,462,976, tertiary amine salt of a glycosaminoglycan (such as hyaluronic acid) is reacted with a photoreactive compound to undergo esterification. The ester product is then exposed to UV radiation to form a crosslinked water-insoluble glycosaminoglycan derivative.

Francesco della Valle et al. at Fidia, S. p. A. in U.S. Pat. No. 4,851,521 discloses a process for preparing esters of hyaluronic acid. Hyaluronic acid is first converted into an ammonium salt that can be dissolved in an organic solvent, and is then reacted with an aliphatic type alcohol to form an ester of hyaluronic acid. An ester linkage is formed by the reaction of the carboxyl group (COOH) in hyaluronic acid and the hydroxy group in the alcohol.

Francesco della Valle et al. in U.S. Pat. No. 4,957,744 discloses a process for preparing cross-linked esters of hyaluronic acid. Hyaluronic acid is first converted into an ammonium salt. Then, a polyhydric alcohol is used to react with more than two carboxyl groups (COOH) in hyaluronic acid, thus forming a cross-linked esterified hyaluronic acid.

Francesco della Valle et al. in U.S. Pat. No. 5,122,598 discloses a process for preparing polysaccharide esters. Polysaccharide, such as carboxymethylcellulose and carboxymethylchitin, is first converted into an ammonium salt. Then, an alcohol is used to react with the carboxyl group (COOH) in hyaluronic acid, thus forming a polysaccharide ester.

Francesco della Valle et al. in U.S. Pat. No. 5,202,431 discloses a process for preparing partial esters of hyaluronic acid. Hyaluronic acid is first converted into an ammonium salt. Then, an aliphatic alcohol is used to react with the carboxyl group (COOH) in hyaluronic acid. Then, the hyaluronic acid ester is salified with a therapeutically active amine.

Francesco della Valle et al. in U.S. Pat. No. 5,336,767 discloses a process for preparing total or partial esters of hyaluronic acid. Hyaluronic acid is first converted into an ammonium salt. Then, a pharmacologically active alcohol, such as cortisone hydrocortisone or prednisone is reacted with the carboxyl group (COOH) in hyaluronic acid via an ester linkage.

Francesco della Valle et al. in U.S. Pat. No. 5,442,053 discloses a composition including hyaluronic acid and a pharmacologically active substance. A hyaluronic acid fraction with a molecular weight between 50,000 and 100,000 is particularly suitable for wound healing and hyaluronic acid with a molecular weight between 500,000 and 730,000 is particularly suitable for intraarticular injection.

Zefferino Righetto et al. in U.S. Pat. No. 5,856,299 discloses highly reactive esters of carboxy polysaccharide and carboxy polysaccharides derived therefrom. Hyaluronic acid is first converted into a salt of hyaluronic acid capable of being dissolved in an organic solvent. Then, an aromatic alcohol is used to react with the carboxy group (COOH) in hyaluronic acid, thus forming a highly reactive esterified hyaluronic acid suitable for biomedical and pharmaceutical fields.

However, there is still a need to modify hyaluronic acid in order to render it improved properties or various applications.

SUMMARY OF THE INVENTION

An object of the present invention is to provide a novel biodegradable hyaluronic acid derivative substituted with a short chain group on the hydroxy position via a urethane linkage.

Another object of the present invention is to provide a novel biodegradable hyaluronic acid derivative grafted with a prepolymer on the hydroxy position via a urethane linkage.

Another object of the present invention is to provide a biodegradable polymeric micelle composition.

A further object of the present invention is to provide a pharmaceutical or bioactive composition including a pharmaceutically active molecule or a bioactive molecule entrapped within the micelles formed by the biodegradable hyaluronic acid derivative.

To achieve the above objects, the biodegradable hyaluronic acid derivative of the present invention includes a modified hyaluronic acid repeating unit represented by the formula (HA)-[O(C=O)NH-M]$_p$, wherein HA is a unit including N-acetyl-D-glucosamine and D-glucuronic acid, M is a modifying moiety containing a $C_{2-16}$ hydrocarbyl group or a prepolymer, and p is an integer of 1 to 4.

The biodegradable polymeric micelle composition of the present invention includes:

a hydrophilic medium; and a biodegradable hyaluronic acid derivative comprising a modified hyaluronic acid repeating unit represented by the formula (HA)-[O(C=O)NH-M]$_p$, wherein HA is a unit including N-acetyl-D-glucomamine and D-glucuronic acid, M is a modifying moiety containing a $C_{2-16}$ hydrocarbyl group or a biodegradable hydrophobic prepolymer, and p is an integer of 1 to 4, wherein the biodegradable hyaluronic acid derivative forms micelles.

The pharmaceutical or bioactive composition of the present invention includes:

a hydrophilic medium;

a biodegradable hyaluronic acid derivative comprising a modified hyaluronic acid repeating unit represented by the formula (HA)-[O(C=O)NH-M]$_p$, wherein HA is unit including N-acetyl-D-glucoamine and D-glucuronic acid, M is a modifying moiety containing $C_{2-16}$ hydrocarbyl group or a biodegradable hydrophobic prepolymer, and p is an integer of 1 to 4; and a pharmaceutically active molecule or a bioactive molecule entrapped within the micelles formed by the biodegradable hyaluronic acid derivative.

BRIEF DESCRIPTION OF THE DRAWINGS

The present invention will become more fully understood from the detailed description given hereinbelow and the accompanying drawings, given by way of illustration only and thus not intended to be limitative of the present invention.

DETAILED DESCRIPTION OF THE INVENTION

Figure 1A:
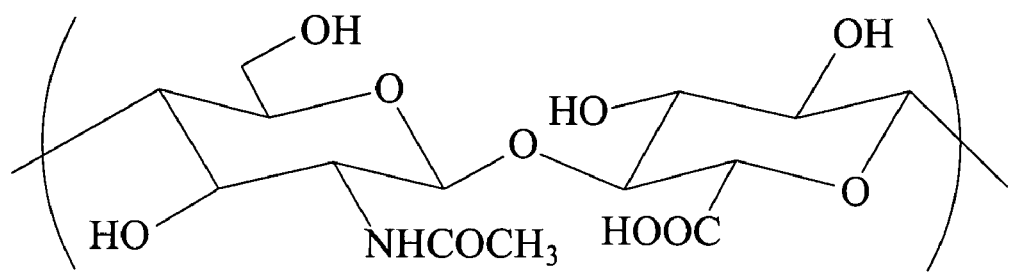
FIG. 1a shows a native hyaluronic acid repeating unit, which is not modified.

The native hyaluronic acid is a linear mucopolysaccharide constituted by N-acetyl-D-glucosamine and D-glucuronic acid repeating units, as shown in FIG. 1a.

The present invention introduces a modifying moiety onto the hydroxy group (—OH) position in the native hyaluronic acid via a urethane linkage [—O(C=O)NH—]. The modifying moiety can contain a $C_{2-16}$ hydrocarbyl group or a prepolymer.

In other words, the modified hyaluronic acid (hyaluronic acid derivative) of the present invention includes a modified hyaluronic acid repeating unit represented by the formula

(HA)-[O(C=O)NH-M]$_p$     (1)

wherein HA is a unit including N-acetyl-D-glucosamine and D-glucuronic acid, M is a modifying moiety containing a $C_{2-16}$ hydrocarbyl group or a prepolymer, and p is 1 to 4.

Figure 1B:
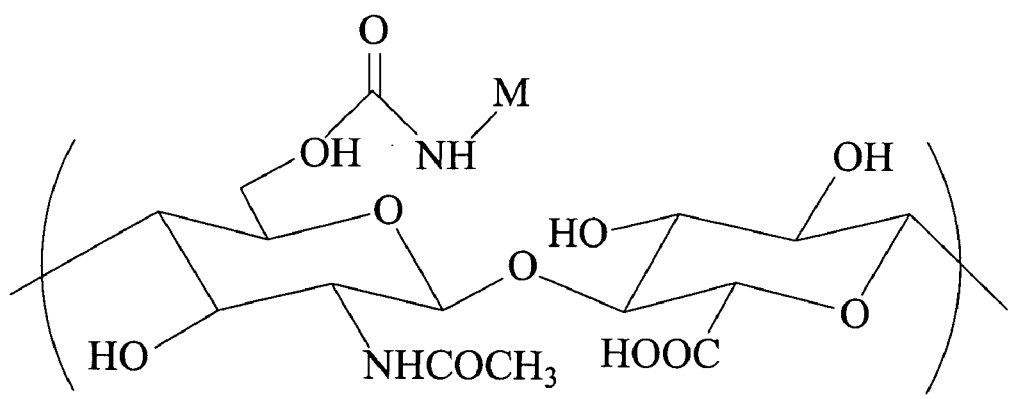
FIG. 1b shows a modified hyaluronic acid repeating unit attached with one modifying moiety (M) via a urethane linkage.

FIG. 1b illustrates the chemical structure of formula (1), in which p is 1.

In the hyaluronic acid derivative of the present invention, the —COOH groups and the —NHCOCH$_3$ groups can remain intact, or, some of the —COOH groups and/or some of the —NHCOCH$_3$ groups can be substituted according to practical requirements. For example, the —COOH group can be converted into a —COOM$_1$ group, wherein M$_1$ can be an alkaline metal, an alkaline earth metal, ammonium, or aluminum. Thus, the salt of the hyaluronic acid derivative of the present invention is within the scope of the present invention.

In addition, according to the present invention, the —OH groups in the native hyaluronic acid can be totally or partially modified. Totally modification means that all of the —OH groups in the native hyaluronic acid are modified via a urethane linkage as described above (p=4).

Figure 1C:
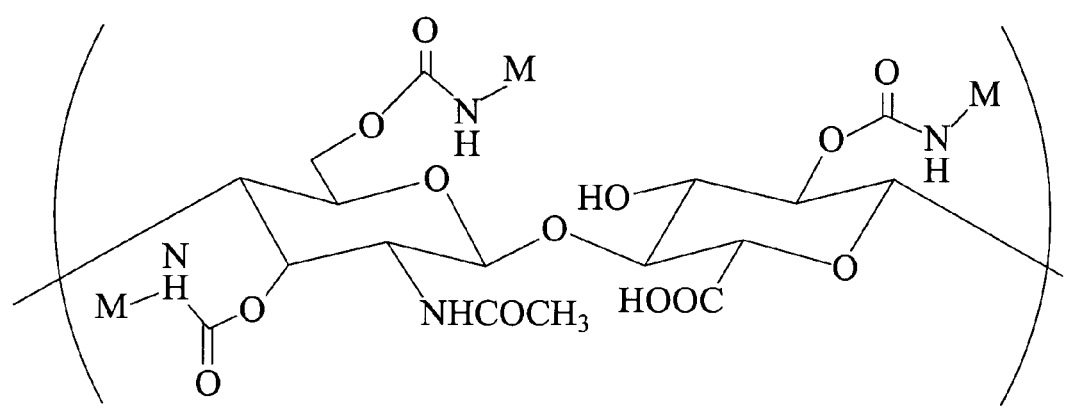
FIG. 1c shows a modified hyaluronic acid repeating unit attached with three modifying moieties (M) via a urethane linkage.

Partially modification means that some of the —OH groups in the native hyaluronic acid are modified, but some are not modified. That is to say, the hyaluronic acid derivative of the present invention can include a plurality of native hyaluronic acid repeating units (p=0, as shown in FIG. 1a) and a plurality of modified hyaluronic acid repeating units. The modified hyaluronic acid repeating units may have different modification extents. That is, the modified hyaluronic acid repeating units with p=1, 2, 3, and 4 may be present in the hyaluronic acid derivative. FIG. 1b shows a modified hyaluronic acid repeating unit attached with one modifying moiety (M) via a urethane linkage (p=1). FIG. 1c shows a modified hyaluronic acid repeating unit attached with three modifying moieties (M) via a urethane linkage (p=3).

In addition, all of the hyaluronic acid repeating units can be modified (that is, no native hyaluronic acid repeating unit remains), but not all of the —OH groups in the native hyaluronic acid are modified. For example, the hyaluronic acid derivative of the present invention can include a first modified hyaluronic acid repeating unit (FIG. 1b, p=1), a second modified hyaluronic acid repeating unit (p=2), a third modified hyaluronic acid repeating unit (FIG. 1c, p=3), a fourth modified hyaluronic acid repeating unit (p=4), or a mixture thereof, but no native hyaluronic acid repeating unit (p=0) is present.

For better understanding, the biodegradable hyaluronic acid derivative of the present invention can be classified into two categories:

(A) a biodegradable hyaluronic acid derivative substituted with a short chain moiety (when M is a modifying moiety containing a $C_{2-16}$ hydrocarbyl group), and (B) a biodegradable hyaluronic acid copolymer grafted with a prepolymer (when M is a modifying moiety containing a prepolymer).

Category (A): Hyaluronic Acid Derivative Substituted with Short Chain Moiety

The hyaluronic acid derivative in category (A) of the present invention includes a modified hyaluronic acid repeating unit represented by the formula

(HA)-[O(C=O)NH-M]$_p$ (1)

wherein HA is a unit including N-acetyl-D-glucosamine and D-glucuronic acid, M is a modifying moiety containing a $C_{2-16}$ hydrocarbyl group, and p is an integer of 1 to 4.

Figure 1D:
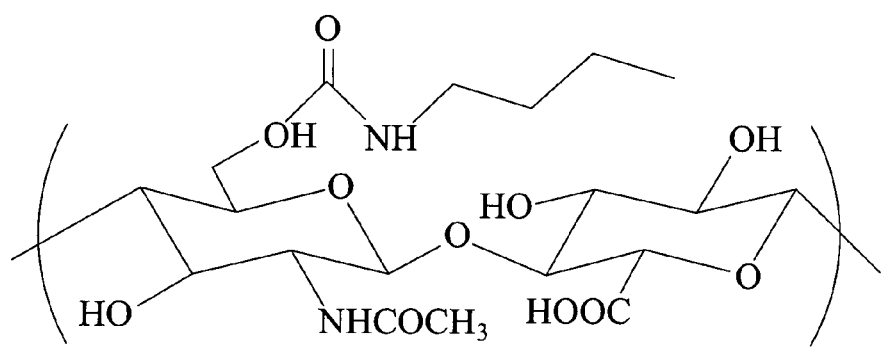
FIG. 1d shows a modified hyaluronic acid repeating unit attached with butyl groups via a urethane linkage.

FIG. 1d illustrates one example of formula (1) in category (A) of the present invention, in which M is butyl and p is 1.

Preferably, M can be a $C_{2-16}$ alkyl group, more preferably a $C_{4-12}$ alkyl group.

The process for preparing the biodegradable hyaluronic acid derivative in category (A) of the present invention is described below. A hyaluronic acid having a hydroxy group (—OH) is reacted with a $C_{2-16}$ hydrocarbyl isocyanate. (The $C_{2-16}$ hydrocarbyl isocyanate can be formed from the reaction of a $C_{2-16}$ alcohol with an isocyante group-containing compound.) Thus, the $C_{2-16}$ hydrocarbyl (short chain moiety) is introduced onto the hydroxy group via a urethane [—O(C=O)—NH—] linkage, forming the biodegradable hyaluronic acid derivative in category (A).

The hyaluronic acid starting material needs not to be a native hyaluronic acid, but can be a hyaluronic acid derivative. That is to say, the starting material can be a hyaluronic acid where the —COOH group or the —NHCOCH$_3$ group is substituted. Also, even the hydroxy group (—OH) in the hyaluronic acid starting material can be partially substituted, as long as there are still residual —OH groups for introducing the short chain moiety via the urethane linkage.

For example, in order to allow the reaction to be performed in an organic solvent, the hyaluronic acid starting material can be a hyaluronic acid salt capable of being dissolved in an organic solvent. For example, the hyaluronic acid having a hydroxy group (starting material) can be a quaternary ammonium salt of hyaluronic acid. That is, the —COOH group in the native hyaluronic acid is converted into a —COONH$_4$ group.

The hyaluronic acid having a hydroxy group (starting material) can have a molecular weight of 2,000 to 3,500,000.

Preferably, the $C_{2-16}$ hydrocarbyl isocyanate (modifying compound) can be a $C_{2-16}$ alkyl isocyanate, and more preferably a $C_{4-12}$ alkyl isocyanate. Representative examples include butyl isocyanate, sec-butyl isocyanate, octyl isocyanate, and dodecyl isocyanate.

The reaction can be conducted at a temperature of 10° C. to 90° C. in the presence of a catalyst such as di-n-butyltin dilaurate, di-n-butyltin diacetate, sodium phenate, ferric chloride, copper acetylacetonate, zinc naphthenate, or tributylphosphine.

Category (B): Hyaluronic Acid Derivative Grafted with Biodegradable Prepolymer

The hyaluronic acid derivative in category (B) of the present invention includes a modified hyaluronic acid repeating unit represented by the formula

(HA)-[O(C=O)NH-M]$_p$ (1)

wherein HA is a unit including N-acetyl-D-glucosamine and D-glucuronic acid, M is a modifying moiety containing a prepolymer, and p is an integer of 1 to 4.

Figure 1E:
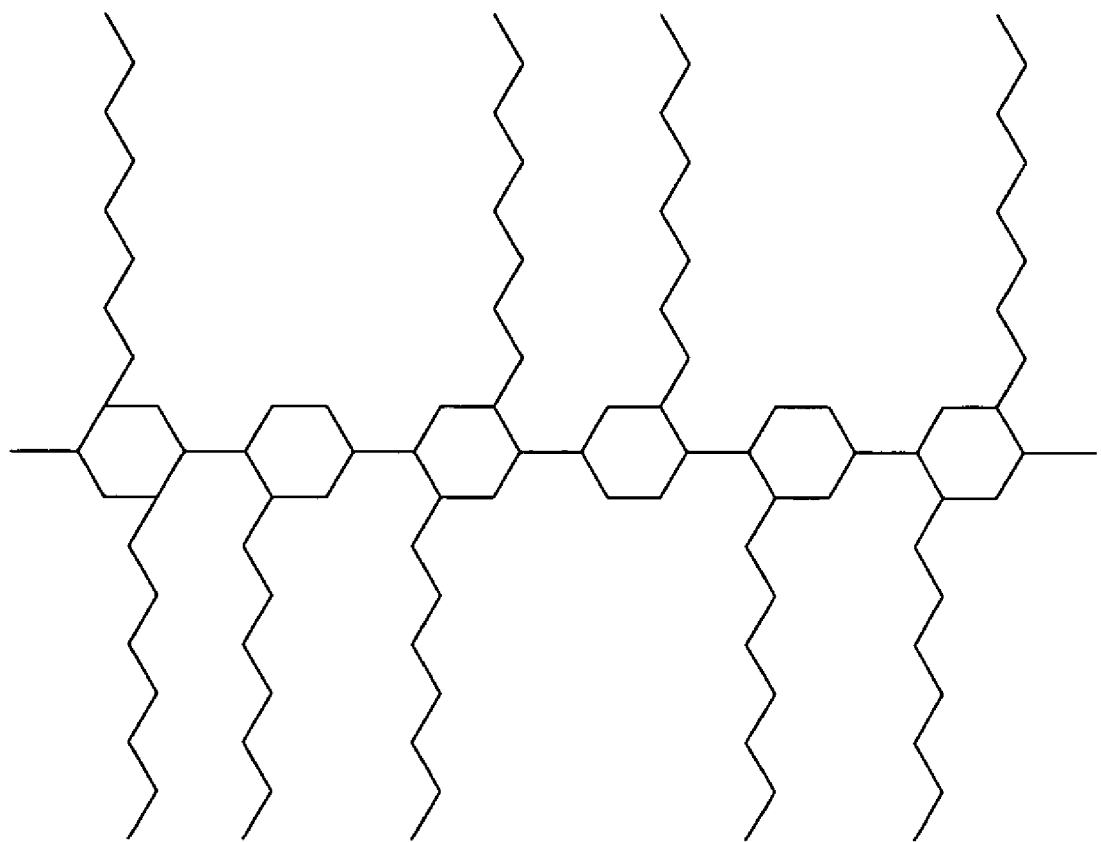
FIG. 1e is a chemical structure of the comb-like shaped hyaluronic acid graft copolymer.

When M is a modifying moiety containing a prepolymer, the hyaluronic acid derivative including a plurality of the formula (1) repeating units can constitute a comb-like, or a brush-like shaped graft copolymer as shown in FIG. 1e.

According to the present invention, the prepolymer grafted onto the —OH position of hyaluronic acid can be hydrophobic, hydrophilic, or amphiphilic. Preferably, the prepolymer suitable for use is biodegradable and can be the same or different. For example, the biodegradable hydrophobic prepolymer can be a biodegradable polyester-containing prepolymer. Representative examples of the suitable biodegradable polyester-containing hydrophobic prepolymers include polycaprolactone (PCL), poly L-lactide (PLLA), polylactic acid (PLA), polyglycolic acid (PGA), poly-lactic-co-glycolic acid copolymer (PLGA copolymer), and polycaprolactone-polylactic acid copolymer (PCL-PLA copolymer).

Representative examples of the biodegradable hydrophilic prepolymers include polyvinylpyrridone, polyethylene glycol, and polyvinylalcohol. Representative examples of the biodegradable amphiphilic prepolymers include polycaprolactone-polyethylene glycol copolymer (PCL-PEG copolymer), polylactic acid-polyethylene glycol copolymer (PLA-PEG copolymer), and polyglycolic acid-polyethylene glycol copolymer (PGA-PEG copolymer).

The biodegradable prepolymer can have a molecular weight of 500 to 200000, preferably 500 to 50000.

The process for preparing the biodegradable hyaluronic acid derivative in category (B) of the present invention is described below. A prepolymer having a hydroxy group is provided. Then, the prepolymer having a hydroxy group is reacted with a diisocyanate compound to form a modifying compound having an isocyanate (—N=C=O) group via a urethane [—O(C=O)—NH—] linkage. Finally, a hyaluronic acid having a hydroxy group (—OH) is reacted with the modifying compound having an isocyanate (—N=C=O) group to form the biodegradable hyaluronic acid derivative in category (B) via a urethane [—O(C=O)—NH—] linkage.

The biodegradable prepolymer grafted onto the —OH position of hyaluronic acid can be the same or different. Different prepolymers can be mixed and then grafted onto the hyaluronic acid at the same time. Or, different prepolymers can be grafted onto the hyaluronic acid sequentially and separately.

The diisocyanate suitable for use in the present invention can be aliphatic type isocyanate, such as hexamethylene diisocyanate or 4,4-methylene-bis(phenylene isocyanate).

The hyaluronic acid starting material needs not to be a native hyaluronic acid, but can be a hyaluronic acid derivative. That is to say, the starting material can be a hyaluronic acid where the —COOH group or the —NHCOCH$_3$ group is substituted. Also, even the hydroxy group (—OH) in the hyaluronic acid starting material can be partially substituted, as long as there are still residual —OH groups for introducing the short chain moiety via the urethane linkage.

For example, in order to perform the reaction in an organic solvent, the hyaluronic acid starting material can be a hyaluronic acid salt capable of being dissolved in an organic solvent. For example, the hyaluronic acid having a hydroxy group (starting material) can be a quaternary ammonium salt of hyaluronic acid. That is, the —COOH group in the native hyaluronic acid is converted into a —COON(Bu)$_4$ group.

The hyaluronic acid having a hydroxy group (starting material) can have a molecular weight of 2,000 to 3,500,000.

The prepolymer suitable for use in the present invention can be biodegradable and can be hydrophobic, hydrophilic, or amphiphilic. The biodegradable prepolymer having a hydroxy group can have a molecular weight of 500 to 200000, preferably 500 to 50000.

Representative examples of the suitable biodegradable hydrophobic prepolymers having a hydroxy group include polycaprolactone (PCL), poly L-lactide (PLLA), polylactic acid (PLA), polyglycolic acid (PGA), poly-lactic-co-glycolic acid copolymer (PLGA copolymer), and polycaprolactone-polylactic acid copolymer (PCL-PLA copolymer). Representative examples of the biodegradable hydrophilic prepolymers having a hydroxy group include polyvinylpyrridone, polyethylene glycol, and polyvinylalcohol. Representative examples of the biodegradable amphiphilic prepolymers having a hydroxy group include polycaprolactone-polyethylene glycol copolymer (PCL-PEG copolymer), polylactic acid-polyethylene glycol copolymer (PLA-PEG copolymer), and polyglycolic acid-polyethylene glycol copolymer (PGA-PEG copolymer).

The reaction can be conducted at a temperature of 10° C. to 90° C. in the presence of a catalyst such as di-n-butyltin dilaurate, di-n-butyltin diacetate, sodium phenate, ferric chloride, copper acetylacetonate, zinc naphthenate, or tributylphosphine.

Biodegradable Polymeric Micelle Composition

The hyaluronic acid derivative, either substituted with short chain moiety ($C_{2-16}$ hydrocarbyl) as described above in category (A) or grafted with a biodegradable hydrophobic prepolymer as described above in category (B), can be dissolved in a hydrophilic medium. Thus, the hyaluronic acid derivative forms micelles.

Figure 2:
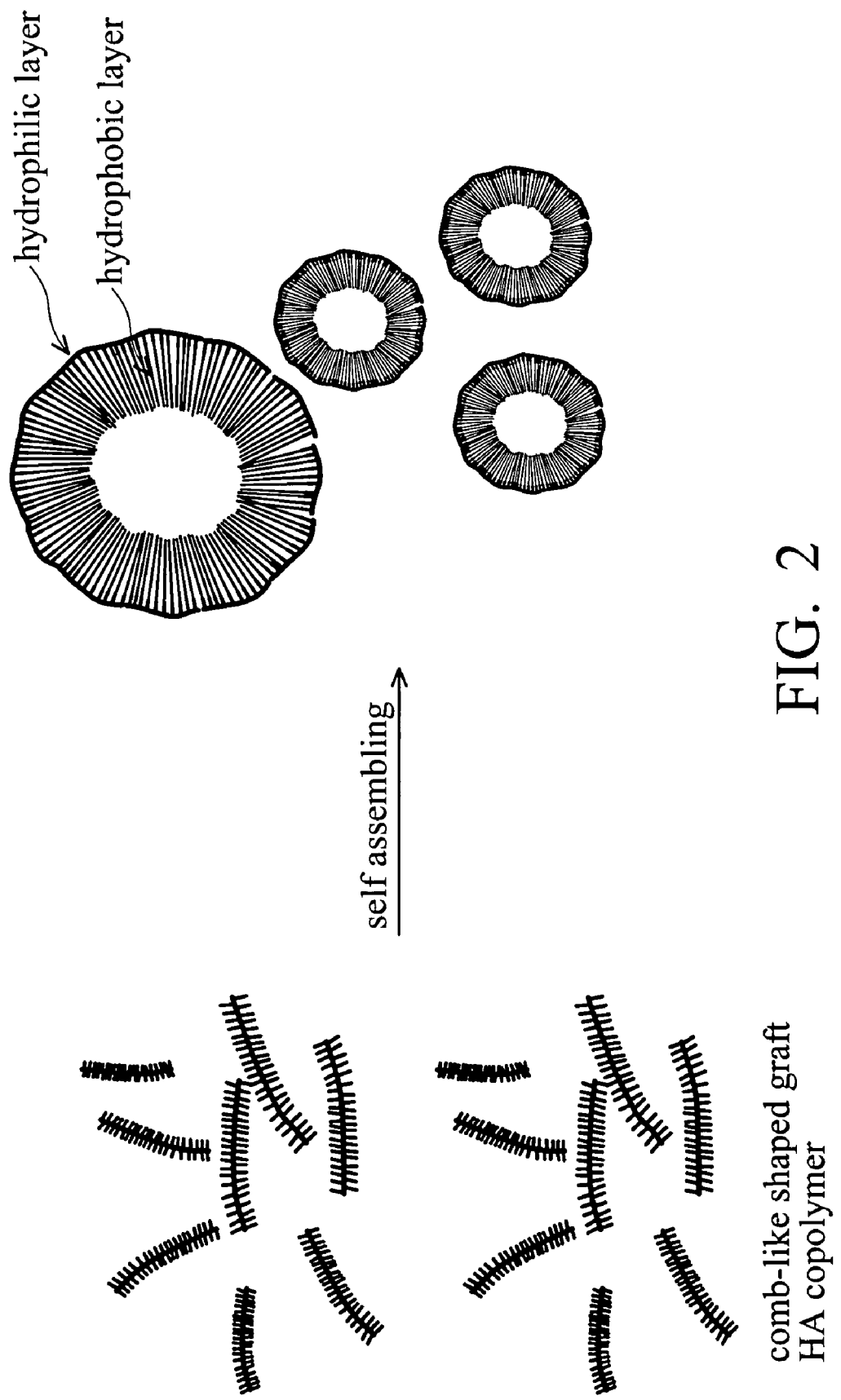
FIG. 2 illustrates the micelles structure of the hyaluronic acid derivative grafted with prepolymer.

For instance, when the biodegradable hyaluronic acid derivative is a comb-like shaped graft copolymer as described above and dissolved in a hydrophilic medium at a concentration higher than a critical micelle concentration, the comb-like shaped graft copolymer is self assembled into micelles. FIG. 2 shows the schematic diagram of the micelles. The hyaluronic acid main chains form an outer hydrophilic layer and the biodegradable hydrophobic prepolymers form an inner hydrophobic layer. A hydrophobic core is formed inside the hydrophobic layer.

In the micelle composition, the hyaluronic acid derivative can have a low critical micelle concentration in the range of 0.005 weight % to 1.0 weight %, preferably 0.005 to 0.5 weight %, most preferably 0.005 to 0.3 weight %. The hyaluronic acid derivative micelles can have a size of 10 nm to 500 nm, preferably of 50 nm to 400 nm, most preferably 50 to 300 nm.

The hydrophilic medium can be water or an aqueous solution.

Pharmaceutical or Bioactive Composition

As described above, the hyaluronic acid derivative, either substituted with short chain moiety (C2-16 hydrocarbyl) as described above in category (A) or grafted with a biodegradable hydrophobic prepolymer as described above in category (B), when dissolved in a hydrophilic medium forms micelles with a hydrophobic core. Therefore, such micelles can be used to entrap a pharmaceutically active molecule or a bioactive molecule.

Thus, the present invention provides a pharmaceutical or bioactive composition including a hydrophilic medium;

a biodegradable hyaluronic acid derivative comprising a modified hyaluronic acid repeating unit represented by the formula

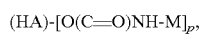

wherein HA is a unit including N-acetyl-D-glucosamine and D-glucuronic acid, M is a modifying moiety containing a $C_{2-16}$ hydrocarbyl group or a biodegradable hydrophobic prepolymer, and p is an integer of 1 to 4; and a pharmaceutically active molecule or a bioactive molecule entrapped within the micelles formed by the biodegradable hyaluronic acid derivative.

Preferably, the biodegradable hyaluronic acid derivative is a comb-like shaped graft copolymer and the pharmaceutically active or bioactive molecule is hydrophobic, such as anti-tumor drugs, anti-rejective drugs, opioid analgesics.

The following examples are intended to illustrate the process and the advantages of the present invention more fully without limiting its scope, since numerous modifications and variations will be apparent to those skilled in the art.

SERIES A EXAMPLES

Hyaluronic Acid Substituted with Short Chain Alkyl

Preparative Example 1

Preparation of Quaternary Ammonium Salt of Hyaluronic Acid 0.5 g of sodium salt of hyaluronic acid was dissolved in 400 ml of deionized water and stirred thoroughly. The solution was then eluted in a 25 cm Dowex 50×8 column in $H^+$ form for ion exchange. The resulting solution was neutralized with 40% tetrabutylammonium hydroxide solution and then freeze-dried. Yield: 0.667 g.

Example A-1

100% Substituted Butyl Urethane Derivative of Hyaluronic Acid (C4-HA)

Figure 3:
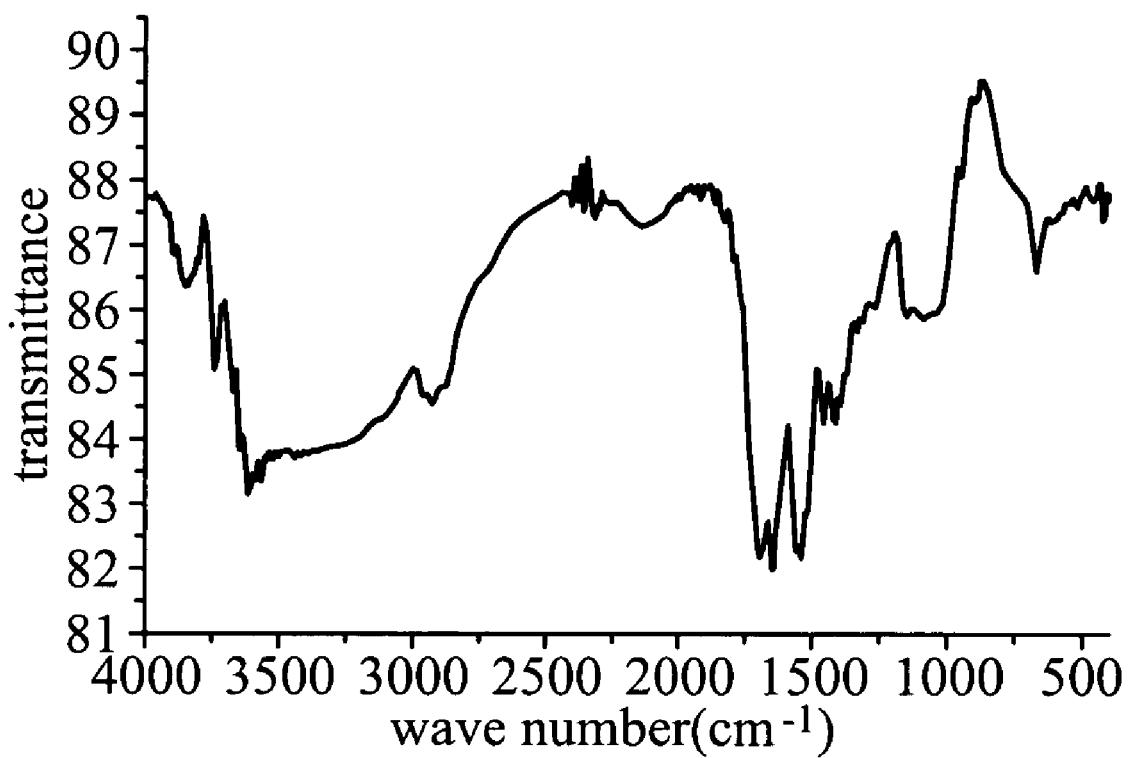
FIG. 3 is the IR spectrum of 100% substituted butyl urethane derivative of hyaluronic acid (C4-HA) prepared from Example A-1.

0.30 g ($3\times10^{-3}$ meq, stoichiometrically 100% substituted) of quaternary ammonium salt of hyaluronic acid prepared from Preparative Example 1 was dissolved in 60 ml of DMSO (dimethylsulfoxide). 0.3 g of butyl isocyanate ($3\times10^{-3}$ meq) and 100 µl of di-n-butyltin dilaurate (catalyst) were added in sequence. The reaction temperature was 65° C. After 8 hours of reaction, DBA (di-butyl amine) was added to stop the reaction. The reaction mixture was dialyzed in saturated sodium chloride aqueous solution with a dialysis membrane (MWCO=12,000-14,000), purified, exchanged from quaternary ammonium salt to sodium salt, and then freeze-dried to obtain C4-HA powder. The IR spectrum is shown in FIG. 3 and the urethane bond at 1710 $cm^{-1}$ can be seen.

Figure 8:
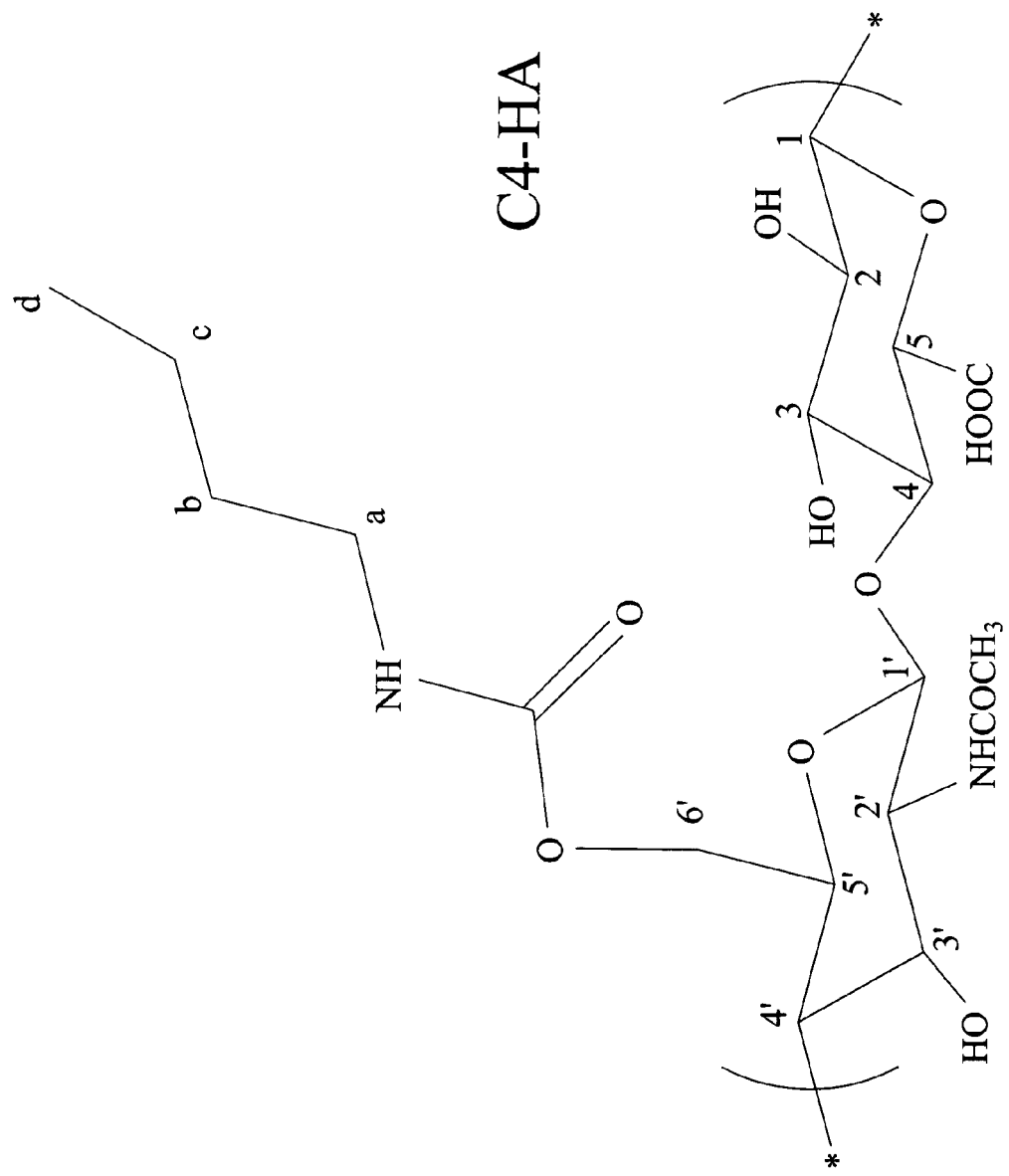
FIG. 8 shows the chemical structure of C4-HA, in which hydrogen positions are labeled a, b, c, and d.

FIG. 8 shows the chemical structure of C4-HA, in which hydrogen positions are labeled a, b, c, and d.

$^1$H NMR of C4-HA:

4.36-2.98 (m, hyaluronic acid backbone), 1.49~1.53 (m, H-a), 1.32~1.35 (m, H-b), 1.18~1.26 (m, H-c), 0.74~0.83 (m, H-d).

Figure 4A:
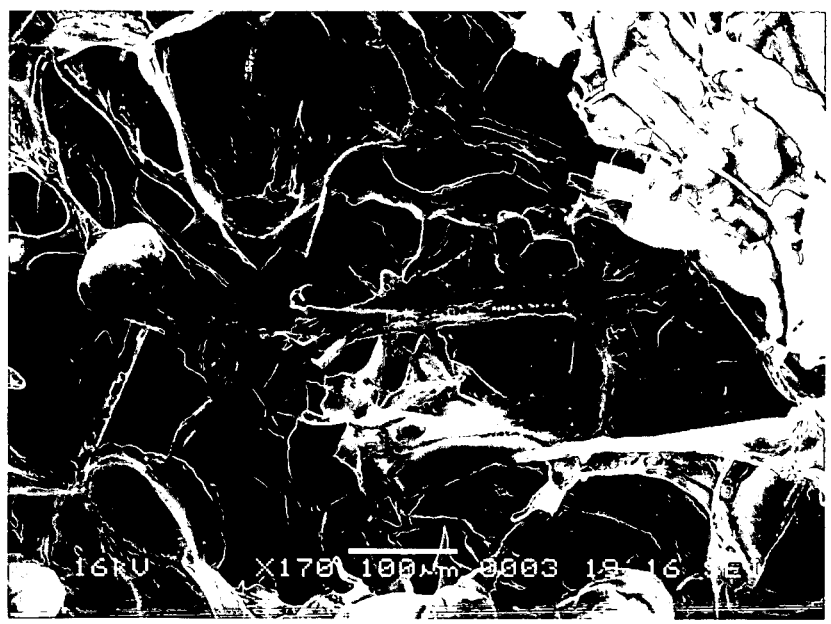
FIGS. 4a and 4b are SEM photographs of the freeze-dried C4-HA prepared from Example A-1.
Figure 4B:
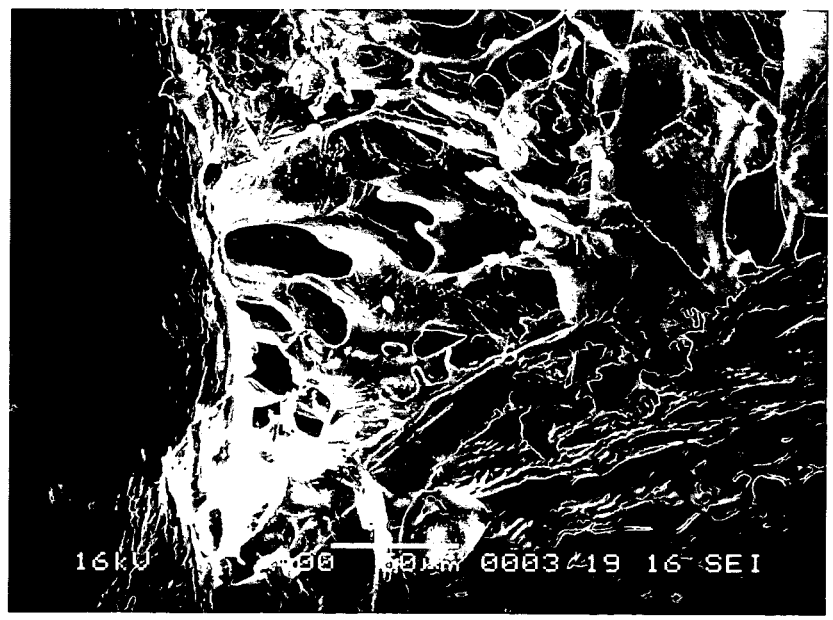

FIGS. 4a and 4b are SEM photographs of the freeze-dried C4-HA (100% substituted butyl urethane derivative of hyaluronic acid). It shows that the hyaluronic acid derivative is porous and suitable for serving as a "scaffold for cell or tissue" (bioresorbable porous matrix).

Figure 5:
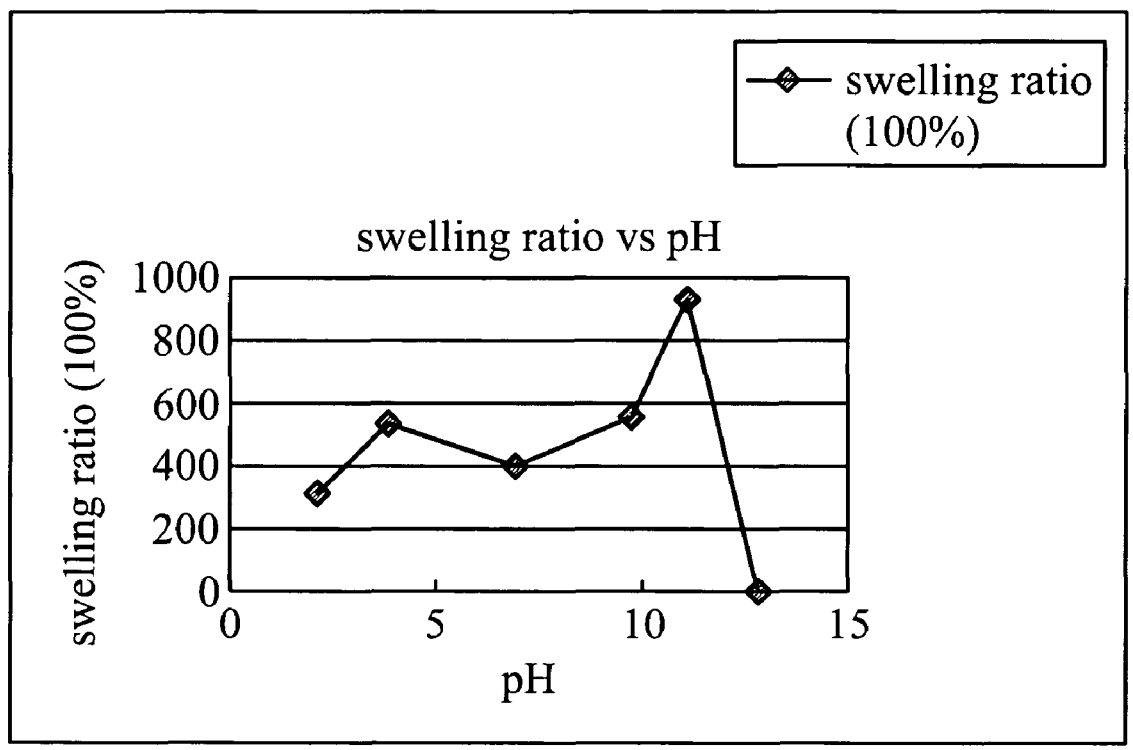
FIG. 5 shows the relationship between the swelling ratio and the pH of C4-HA prepared from Example A-1.

FIG. 5 shows the relationship between the swelling ratio and the pH of C4-HA.

Cytotoxicity Test:

C4-HA was assessed for cytotoxicity using L929 cell line according to the ASTM F895 method. Cell line L929 was cultured in a 6-well culture plate. After 24 hours, a confluent monolayer was formed. Culture supernatant was removed from the plate and then 2 ml of agar medium was spread on the cells for solidification. The C4-HA powder was spread on a circle zone (diameter=1 cm) in the middle of the culture plate, incubated in a $CO_2$ incubator at 37° C. for 1 day, and then assessed for cytotoxicity by the neutral red dye method. The response index=zone index/lysis index. Zone index=0 indicates that there is no detected zone adjacent to or in the specimen. The result shows that the C4-HA material had no cytotoxicity response.

Example A-2

100% Substituted Sec-Butyl Urethane Derivative of Hyaluronic Acid 0.30 g ($3\times10^{-3}$ meq, stoichiometrically 100% substituted) of quaternary ammonium salt of hyaluronic acid prepared from Preparative Example 1 was dissolved in 60 ml of DMSO. 0.3 g of sec-butyl isocyanate ($3\times10^{-3}$ meq) and 100 µl of di-n-butyltin dilaurate (catalyst) were added in sequence. The reaction temperature was 65° C. After 8 hours of reaction, DBA was added to stop the reaction. The reaction mixture was dialyzed in saturated sodium chloride aqueous solution with a dialysis membrane (MWCO=12,000-14,000), purified, exchanged from quaternary ammonium salt to sodium salt, and then freeze-dried.

Example A-3

100% Substituted Octyl Urethane Derivative of Hyaluronic Acid 0.37 g ($3.7\times10^{-3}$ meq) of quaternary ammonium salt of hyaluronic acid prepared from Preparative Example 1 was dissolved in 60 ml of DMSO. 0.58 g of octyl isocyanate ($3.7\times10^{-3}$ meq) and 100 µl of di-n-butyltin dilaurate (catalyst) were added in sequence. The reaction temperature was 65° C. After 8 hours of reaction, DBA was added to stop the reaction. The reaction mixture was dialyzed in saturated sodium chloride aqueous solution with a dialysis membrane (MWCO=12,000-14,000), purified, exchanged from quaternary ammonium salt to sodium salt, and then freeze-dried.

Example A-4

50% Substituted Octyl Urethane Derivative of Hyaluronic Acid 0.37 g ($3.7\times10^{-3}$ meq) of quaternary ammonium salt of hyaluronic acid prepared from Preparative Example 1 was dissolved in 60 ml of DMSO. 0.29 g of octyl isocyanate ($1.85\times10^{-3}$ meq) and 100 µl of di-n-butyltin dilaurate (catalyst) were added in sequence. The reaction temperature was 65° C. After 8 hours of reaction, DBA was added to stop the reaction. The reaction mixture was dialyzed in saturated sodium chloride aqueous solution with a dialysis membrane (MWCO=12,000-14,000), purified, exchanged from quaternary ammonium salt to sodium salt, and then freeze-dried.

Example A-5

10% Substituted Octyl Urethane Derivative of Hyaluronic Acid 0.37 g ($3.7\times10^{-3}$ meq) of quaternary ammonium salt of hyaluronic acid prepared from Preparative Example 1 was dissolved in 60 ml of DMSO. 0.058 g of octyl isocyanate ($3.7\times10^{-4}$ meq) and 100 µl of di-n-butyltin dilaurate (catalyst) were added in sequence. The reaction temperature was 65° C. After 8 hours of reaction, DBA was added to stop the reaction. The reaction mixture was dialyzed in saturated sodium chloride aqueous solution with a dialysis membrane (MWCO=12,000-14,000), purified, exchanged from quaternary ammonium salt to sodium salt, and then freeze-dried.

Example A-6

100% Substituted Dodecyl Urethane Derivative of Hyaluronic Acid (C12-HA)

0.35 g ($3.54\times10^{-3}$ meq) of quaternary ammonium salt of hyaluronic acid prepared from Preparative Example 1 was dissolved in 100 ml of DMSO. 0.75 g of dodecyl isocyanate ($3.54\times10^{-3}$ meq) and 100 µl of di-n-butyltin dilaurate (catalyst) were added in sequence. The reaction temperature was 65° C. After 8 hours of reaction, DBA was added to stop the reaction. The reaction mixture was dialyzed in saturated sodium chloride aqueous solution with a dialysis membrane (MWCO=12,000-14,000), purified, exchanged from quaternary ammonium salt to sodium salt, and then freeze-dried.

Figure 9:
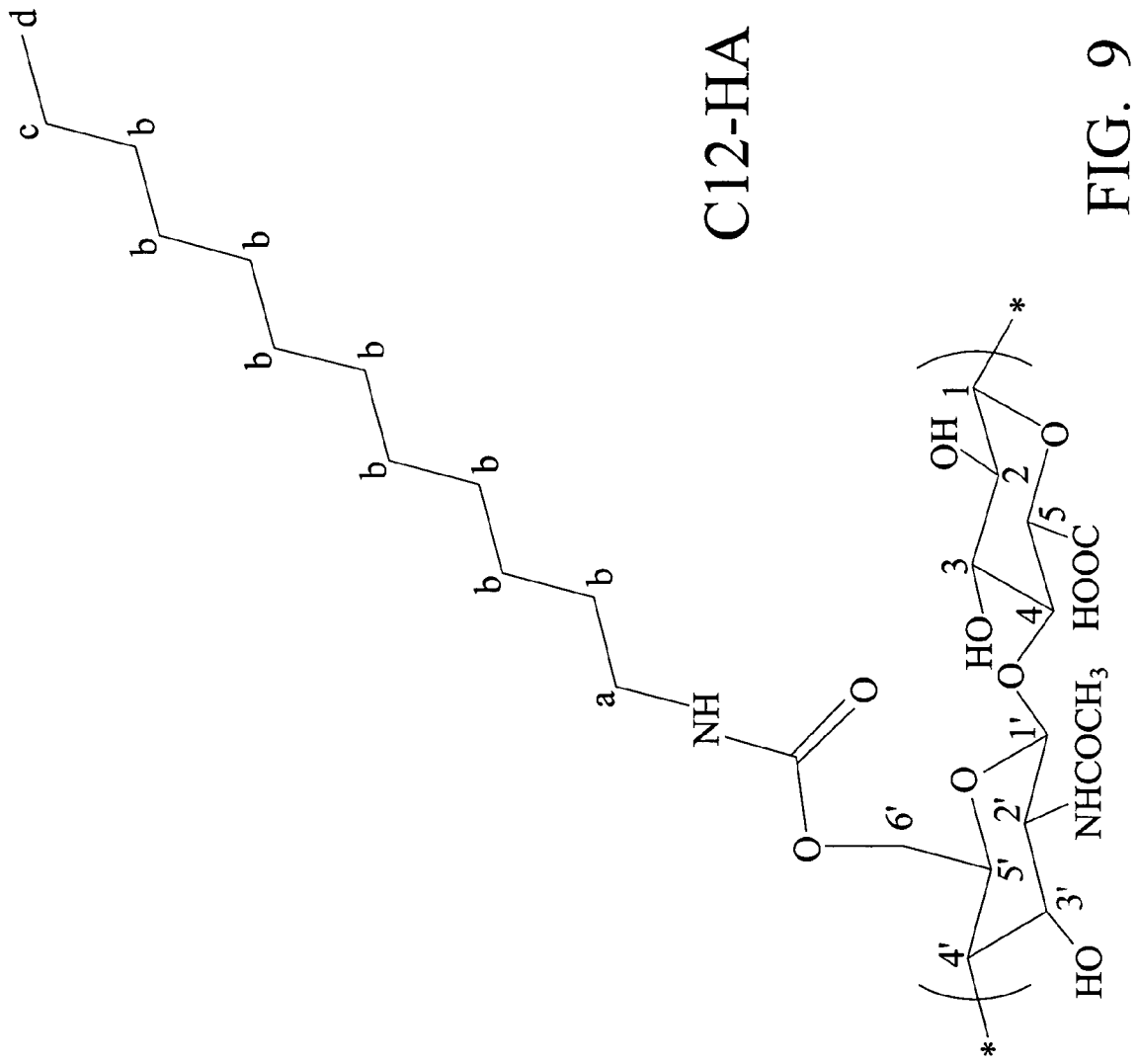
FIG. 9 shows the chemical structure of C12-HA, in which hydrogen positions are labeled a, b, c, and d.

FIG. 9 shows the chemical structure of C12-HA, in which hydrogen positions are labeled a, b, c, and d.

$^1$H NMR of C12-HA:

δ=4.36~2.98 (m, hyaluronic backbone), 1.49~1.53 (m, H-a), 1.32~1.35 (m, H-b), 1.18~1.26 (m, H-c), 0.74~0.83 (m, H-d).

Example A-7

50% Substituted Dodecyl Urethane Derivative of Hyaluronic Acid 0.35 g ($3.54\times10^{-3}$ meq) of quaternary ammonium salt of hyaluronic acid prepared from Preparative Example 1 was dissolved in 100 ml of DMSO. 0.375 g of dodecyl isocyanate ($1.77\times10^{-3}$ meq) and 100 µl of di-n-butyltin dilaurate (catalyst) were added in sequence. The reaction temperature was 65° C. After 8 hours of reaction, DBA was added to stop the reaction. The reaction mixture was dialyzed in saturated sodium chloride aqueous solution with a dialysis membrane (MWCO=12,000-14,000), purified, exchanged from quaternary ammonium salt to sodium salt, and then freeze-dried.

Example A-8

10% Substituted Dodecyl Urethane Derivative of Hyaluronic Acid 0.35 g ($3.54\times10^{-3}$ meq) of quaternary ammonium salt of hyaluronic acid prepared from Preparative Example 1 was dissolved in 100 ml of DMSO. 0.075 g of dodecyl isocyanate ($3.54\times10^{-4}$ meq) and 100 µl of di-n-butyltin dilaurate (catalyst) were added in sequence. The reaction temperature was 65° C. After 8 hours of reaction, DBA was added to stop the reaction. The reaction mixture was dialyzed in saturated sodium chloride aqueous solution with a dialysis membrane (MWCO=12,000-14,000), purified, exchanged from quaternary ammonium salt to sodium salt, and then freeze-dried.

Series B Examples

Hyaluronic Acid Grafted with Prepolymer

Preparative Example 2

Synthesis of Mono-Functional Polycaprolactone (PCL)

Figure 6:
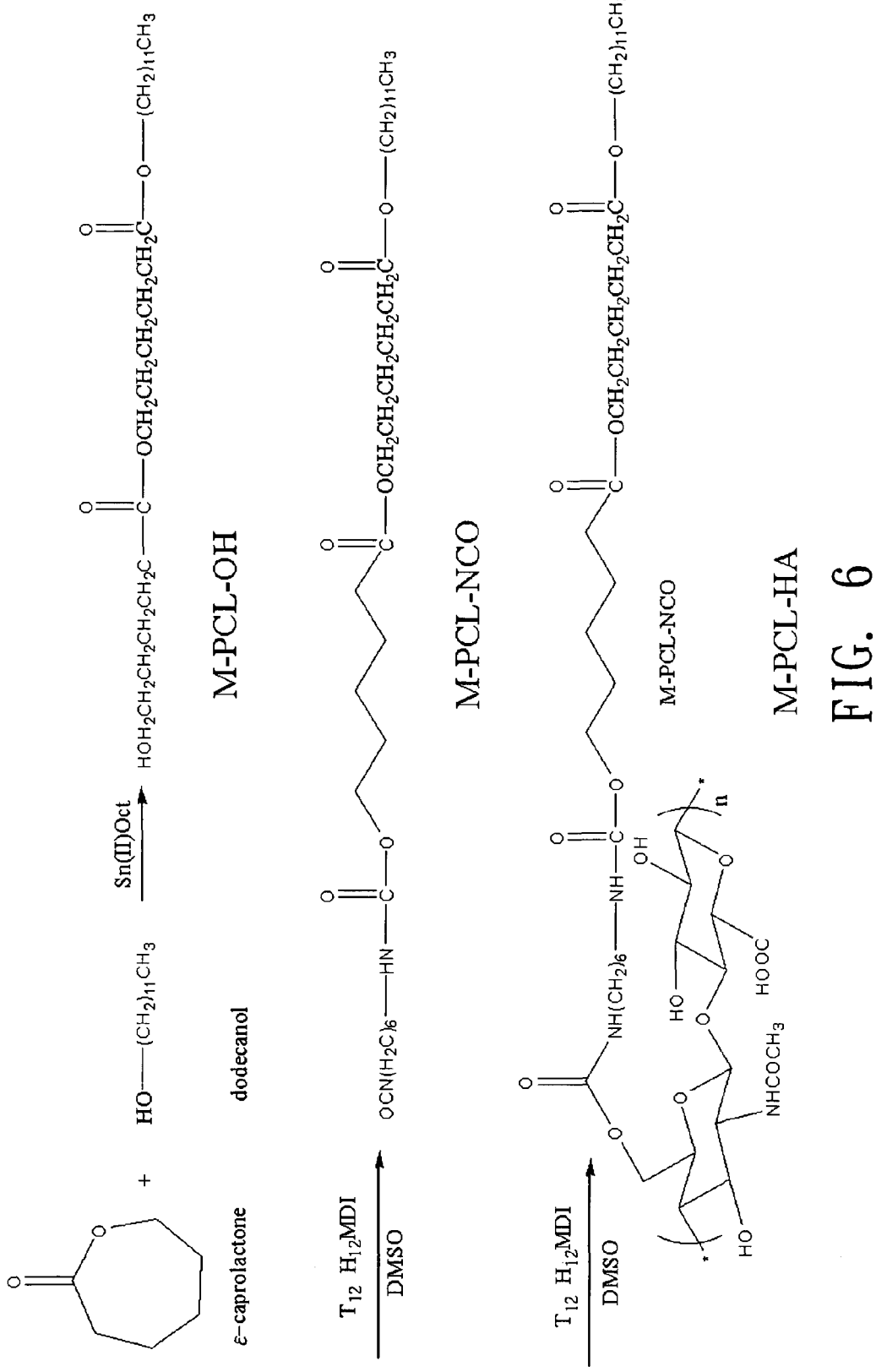
FIG. 6 shows the synthesis pathway of preparing hyaluronic acid copolymer grafted with PCL prepolymer.

200 g (1.75 mole) of caprolactone monomer was placed in a reaction vessel and 32.65 g (0.175 mole) of 1-dodecanol (initiator) and 0.71 g ($1.75 \times 10^{-3}$ mole) of stannous octanoate (catalyst) were then added. The reaction temperature was 120° C. and the reaction time was 2 hours. The reaction mixture was dissolved with chloroform and then poured into ether for reprecipitation. The synthesis pathway is shown in FIG. 6 and the repeating number in this figure, taking for an example, is 2. The GPC (gel permeation chromatography) analysis shows that Mn is 2352, Mw is 3012, and PDI (Mw/Mn) is 1.28.

Figure 10:
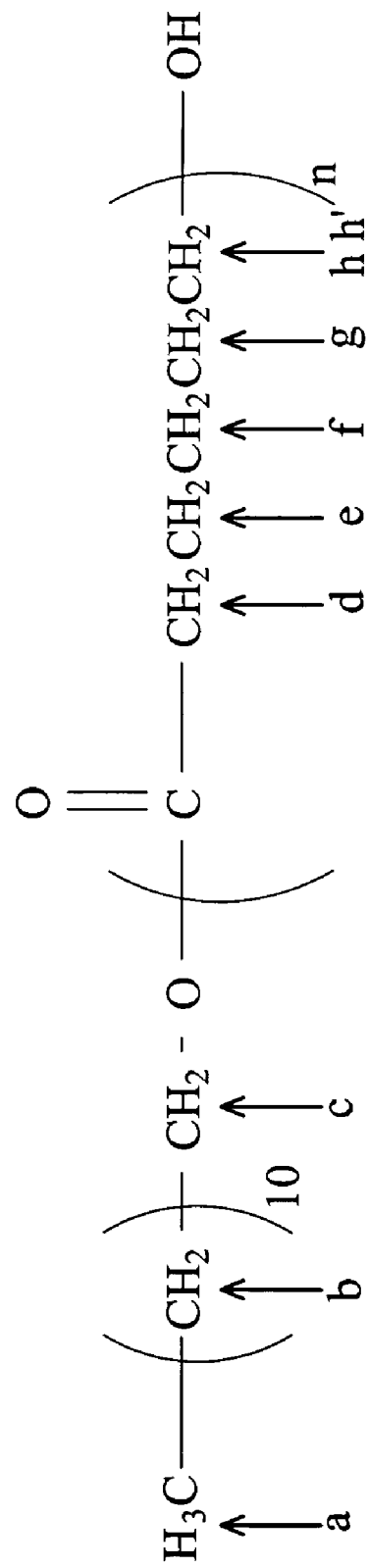
FIG. 10 shows the chemical structure of mono-functional PCL, in which hydrogen positions are labeled a, b, c, d, e, f, g, h and h'.

FIG. 10 shows the chemical structure of mono-functional PCL, in which hydrogen positions are labeled a, b, c, d, e, f, g, h and h'.

NMR Data: PCL:
$\delta$ 0.76 (t, J=7.0 Hz, H-a), 1.16 (S, H-b), 3.96 (t, J=6.8 Hz, H-c), 2.20 (t, J=7.4 Hz, H-d), 1.56 (m, H-e, g), 1.30 (m, H-f), 3.96 (t, J=6.8 Hz, H-h), 3.53 (t, J=7.0 Hz, H-h).

Preparative Example 3

Synthesis of Mono-Functional Poly L-Lactide (PLLA)

200 g (1.39 mole) of lactide monomer was placed in a reaction vessel and 25.82 g (0.139 mole) of 1-dodecanol (initiator) and 0.562 g ($1.39 \times 10^{-3}$ mole) of stannous octanoate (catalyst) were then added. The reaction temperature was 120° C. and the reaction time was 2 hours. The reaction mixture was dissolved with chloroform and then poured into ether for reprecipitation. The GPC analysis shows that Mn is 2189, Mw is 2797, and PDI (Mw/Mn) is 1.28.

Figure 11:
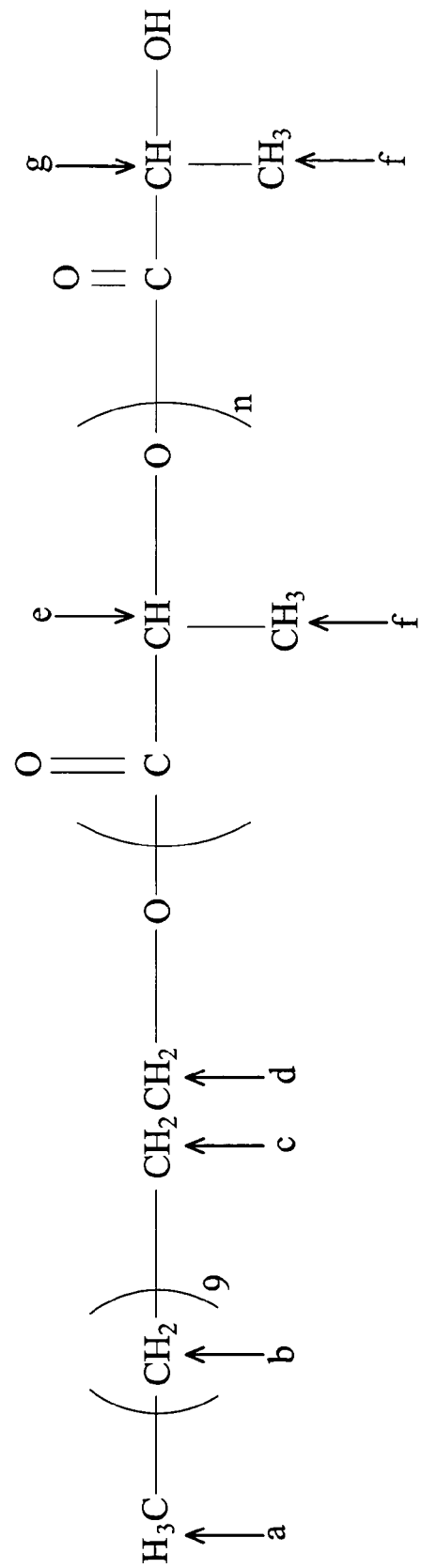
FIG. 11 shows the chemical structure of mono-functional PLLA, in which hydrogen positions are labeled a, b, c, d, e, f, and g.

FIG. 11 shows the chemical structure of mono-functional PLLA, in which hydrogen positions are labeled a, b, c, d, e, f, and g.

NMR Data:
PLLA: $\delta$ 0.76 (t, J=7.0 Hz, H-a), 1.14 (S, H-b), 1.38 (m, H-c), 4.01 (m, H-d), 5.06 (m, H-e), 1.47 (d, J=7.2 Hz, H-f), 4.24 (m, H-g).

Example B-1

Synthesis of Hyaluronic Acid Copolymer Grafted with PCL Prepolymer ($HA_{220,000}$-g-100%-$PCL_{2,300}$ Copolymer)

5.75 g ($2.5 \times 10^{-3}$ mole) of mono-functional PCL (M-PCL-OH) (Mw=2300) prepared from Preparative Example 2 was dissolved in 50 ml of NMP, and then 0.42 g of hexamethylene diisocyanate($H_{12}$MDI) ($2.5 \times 10^{-3}$ mole) and 100 μl of di-n-butyltin dilaurate were added in sequence. The reaction temperature was 60° C. and the reaction time was 5 hours. After reaction, 1 g ($2.5 \times 10^3$ mole) of quaternary ammonium salt of hyaluronic acid (Mw=220,000) was dissolved in 150 ml of DMSO and added to the above PCL solution. 100 μl of di-n-butyltin dilaurate was then added. The reaction temperature was 60° C. After 12 hours of reaction, DBA was added to stop the reaction, obtaining $HA_{220,000}$-g-100%-$PCL_{2,300}$ copolymer. The reaction mixture was dialyzed in saturated sodium chloride aqueous solution with a dialysis membrane (MWCO=3500), purified, exchanged from quaternary ammonium salt to sodium salt, and then freeze-dried. The synthesis pathway is shown in FIG. 6.

Figure 12:
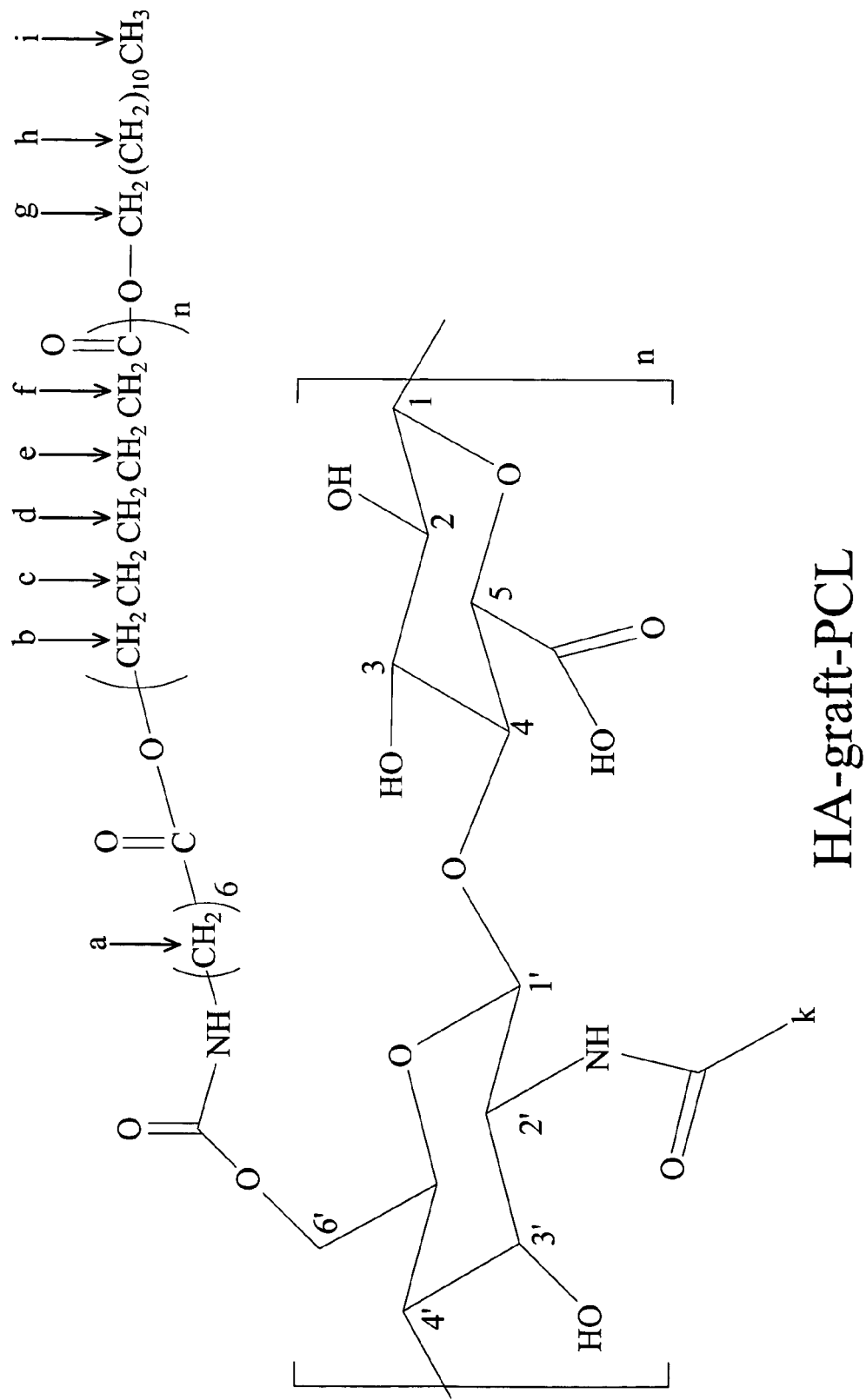
FIG. 12 shows the chemical structure of HA-graft-PCL, in which hydrogen positions are labeled a, b, c, d, e, f, g, h, i, and k.

FIG. 12 shows the chemical structure of HA-graft-PCL, in which hydrogen positions are labeled a, b, c, d, e, f, g, h, i and k.

NMR Data:
$\delta$4.58 (m, H-1), 4.49 (m, H-1'), 4.07 (m, H-2), 3.21 (m, H-2'), 3.94 (m, H-3), 3.60 (m, H-3), 3.52 (m, H-4), 3.60 (m, H-4'), 3.36 (m, H-5), 3.52 (m, H-5'), 4.16 (m, H-6a), 3.92 (m, H-6b), 2.28 (m, H-f), 3.90 (m, H-b), 1.60 (m, H-c, e), 1.45 (m, H-d), 3.89 (m, H-g), 1.40 (m, H-h), 0.86 (m, H-i), 2.03 (s, H-k).

Figure 7:
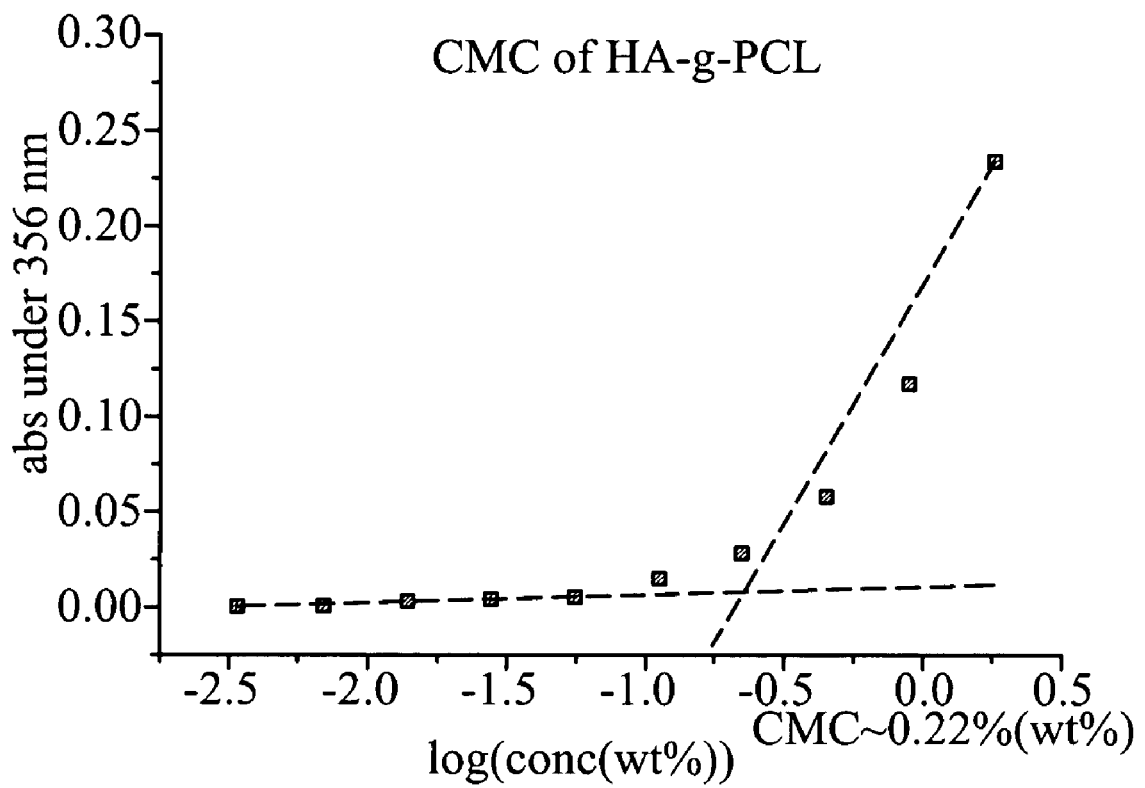
FIG. 7 shows the result of critical micelle concentration (CMC) determination for hyaluronic acid copolymer grafted with PCL prepolymer prepared from Example B-1.

Determination of Critical Micelle Concentration (CMC):
The $HA_{220,000}$-g-100%-$PCL_{2,300}$ copolymer was dissolved in 4 μM diphenyl hexatriene (DPH) solution at a concentration of 0.001%, 0.005%, 0.01%, 0.025%, 0.05%, 0.1%, 0.5%, and 1% respectively. Absorbance at 356 nm wavelength was measured with UV-VIS spectrometer. The result was shown in FIG. 7 and the CMC was 0.22 wt %.

Example B-2

Synthesis of Hyaluronic Acid Copolymer Grafted with PCL Prepolymer ($HA_{220,000}$-g-10%-$PCL_{2,300}$ Copolymer)

0.58 g ($2.5 \times 10^{-4}$ mole) of mono-functional PCL (Mw=2300) was dissolved in 50 ml of NMP, and then 0.042 g of hexamethylene diisocyanate ($H_{12}$MDI) ($2.5 \times 10^{-4}$ mole) and 100 μl of di-n-butyltin dilaurate were added in sequence. The reaction temperature was 60° C. and the reaction time was 5 hours. After reaction, 1 g ($2.5 \times 10^{-3}$ mole) of quaternary ammonium salt of hyaluronic acid (Mw=220,000) was dissolved in 150 ml of DMSO and added to the above PCL solution. 100 μl of di-n-butyltin dilaurate was then added. The reaction temperature was 60° C. After 12 hours of reaction, DBA was added to stop the reaction, obtaining $HA_{220,000}$-g-10%-$PCL_{2,300}$ copolymer. The reaction mixture was dialyzed in saturated sodium chloride aqueous solution with a dialysis membrane (MWCO=3500), purified, exchanged from quaternary ammonium salt to sodium salt, and then freeze-dried.

NMR data of HA-PCL:
$\delta$ 4.58 (m, H-1), 4.49 (m, H-1'), 4.07 (m, H-2), 3.21 (m, H-2'), 3.94 (m, H-3), 3.60 (m, H-3'), 3.52 (m, H-4), 3.60 (m, H-4'), 3.36 (m, H-5), 3.52 (m, H-5'), 4.16 (m, H-6a), 3.92 (m, H-6b), 2.28 (m, H-f), 3.90 (m, H-b), 1.60 (m, H-c, e), 1.45 (m, H-d), 3.89 (m, H-g), 1.40 (m, H-h), 0.86 (m, H-i), 2.03 (s, H-k).

Cytotoxicity Test:
L929-mouse fibroblast cell line was cultured in a 24-well plate at a density of $1 \times 10^5$ cell/ml at 37° C. in a humidified 5% $CO_2$/air incubator. After 24 hours, a confluent monolayer was formed.

UV-sterilized HA-PCL copolymer (10% grafting ratio) powder was dissolved in the culture medium to prepare various solutions with concentration ranging from $10^{-5}$ up to $10^{-2}$ g/ml.

Culture medium was removed and then 2 ml of the various HA-PCL-containing medium was added following continuous exposure for 1 day. The cell viability was analyzed by the MTT colorimetric assay. The results show that the HA-PCL copolymer micelles at various concentrations had no cytotoxicity response.

The MTT chlorimetric assay: Culture medium was removed and then washed three times with PBS (phosphate buffered saline). 5 mg/ml MTT was added to each well and then incubated at 37° C. for 3 hours. A equal volume of blocking solution (DMSO:SDS:medium (1:1:1)) was added for another 20 minutes. The fluid content of each well was transferred to the testing cuvette. The absorbances were measured at 560 nm wavelength. A higher absorbance indicates a higher viability.

Determination of Critical Micelle Concentration (CMC):

The $HA_{220,000}$-g-1.0%-$PCL_{2,300}$ copolymer was dissolved in 4 μM diphenyl hexatriene (DPH) solution at a concentration of 0.001%, 0.005%, 0.01%, 0.025%, 0.05%, 0.1%, 0.5%, and 1% respectively. Absorbance at 356 nm wavelength was measured with UV-VIS spectrometer. The CMC was 0.0851 wt %.

Example B-3

Synthesis of Hyaluronic Acid Copolymer Grafted with PCL Prepolymer ($HA_{50,000}$-g-20%-$PCL_{10,000}$ Copolymer)

1 g ($1 \times 10^{-4}$ mole) of mono-functional PCL (Mw=10000) was dissolved in 100 ml of NMP, and then 0.017 g of hexamethylene diisocyanate ($1 \times 10^{-4}$ mole) and 100 μl of di-n-butyltin dilaurate were added in sequence. The reaction temperature was 60° C. and the reaction time was 5 hours. After reaction, 0.2 g ($2.5 \times 10^{-3}$ mole) of quaternary ammonium salt of hyaluronic acid (Mw=50,000) was dissolved in 100 ml of DMSO and added to the above PCL solution. 100 μl of di-n-butyltin dilaurate was then added. The reaction temperature was 60° C. After 12 hours of reaction, DBA was added to stop the reaction, obtaining $HA_{50,000}$-g-20%-$PCL_{10,000}$ copolymer. The reaction mixture was dialyzed in saturated sodium chloride aqueous solution with a dialysis membrane (MWCO=3500), purified, exchanged from quaternary ammonium salt to sodium salt, and then freeze-dried.

NMR data of HA-PCL:

δ 4.58 (m, H-1), 4.49 (m, H-1'), 4.07 (m, H-2), 3.21 (m, H-2'), 3.94 (m, H-3), 3.60 (m, H-3'), 3.52 (m, H-4), 3.60 (m, H-4'), 3.36 (m, H-5), 3.52 (m, H-5'), 4.16 (m, H-6a), 3.92 (m, H-6b), 2.28 (m, H-f), 3.90 (m, H-b), 1.60 (m, H-c, e), 1.45 (m, H-d), 3.89 (m, H-g), 1.40 (m, H-h), 0.86 (m, H-i), 2.03 (s, H-k).

Example B-4

Synthesis of Hyaluronic Acid Copolymer Grafted with PCL Prepolymer ($HA_{50,000}$-g-100%-$PCL_{2,300}$ Copolymer)

1.15 g ($5 \times 10^{-4}$ mole) of mono-functional PCL (Mw=2300) was dissolved in 50 ml of NMP, and then 0.084 g of hexamethylene diisocyanate ($5 \times 10^{-4}$ mole) and 100 μl of di-n-butyltin dilaurate were added in sequence. The reaction temperature was 60° C. and the reaction time was 5 hours. After reaction, 0.2 g ($5 \times 10^{-4}$ mole) of quaternary ammonium salt of hyaluronic acid (Mw=50,000) was dissolved in 100 ml of DMSO and added to the above PCL solution. 100 μl of di-n-butyltin dilaurate was then added. The reaction temperature was 60° C. After 12 hours of reaction, DBA was added to stop the reaction, obtaining $HA_{50,000}$-g-100%-$PCL_{2,300}$ copolymer. The reaction mixture was dialyzed in saturated sodium chloride aqueous solution with a dialysis membrane (MWCO=3500), purified, exchanged from quaternary ammonium salt to sodium salt, and then freeze-dried.

Determination of Critical Micelle Concentration (CMC):

The $HA_{50,000}$-g-100%-$PCL_{2,300}$ copolymer was dissolved in 4 μM diphenyl hexatriene (DPH) solution at a concentration of 0.001%, 0.005%, 0.01%, 0.025%, 0.05%, 0.1%, 0.5%, and 1% respectively. Absorbance at 356 nm wavelength was measured with UV-VIS spectrometer. The CMC was 0.0794 wt %.

Example B-5

Synthesis of Hyaluronic Acid Copolymer Grafted with PCL Prepolymer ($HA_{220,000}$-g-100%-$PLLA_{2,300}$ Copolymer)

5.75 g ($2.5 \times 10^{-3}$ mole) of mono-functional PLLA (Mw=2300) was dissolved in 50 ml of NMP, and then 0.42 g of hexamethylene diisocyanate ($2.5 \times 10^{-3}$ mole) and 100 μl of di-n-butyltin dilaurate were added in sequence. The reaction temperature was 60° C. and the reaction time was 5 hours. After reaction, 1 g ($2.5 \times 10^{-3}$ mole) of quaternary ammonium salt of hyaluronic acid (Mw=220,000) was dissolved in 150 ml of DMSO and added to the above PLLA solution. 100 μl of di-n-butyltin dilaurate was then added. The reaction temperature was 60° C. After 12 hours of reaction, DBA was added to stop the reaction, obtaining $HA_{220,000}$-g-100%-$PLLA_{2,300}$ copolymer. The reaction mixture was dialyzed in saturated sodium chloride aqueous solution with a dialysis membrane (MWCO=3500), purified, exchanged from quaternary ammonium salt to sodium salt, and then freeze-dried.

Figure 13:
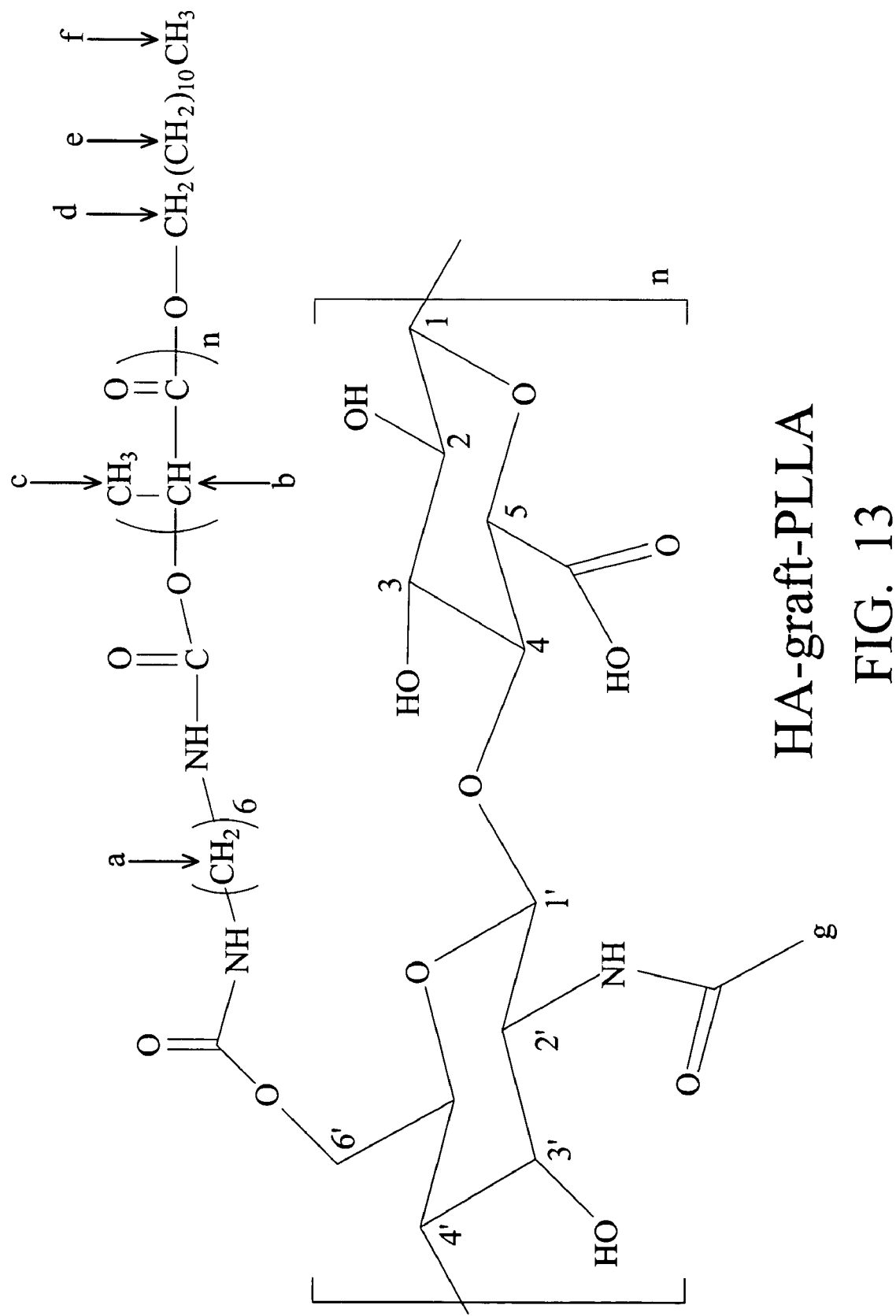
FIG. 13 shows the chemical structure of HA-graft-PLLA, in which hydrogen positions are labeled a, b, c, d, e, f, and g.

FIG. 13 shows the chemical structure of HA-graft-PLLA, in which hydrogen positions are labeled a, b, c, d, e, f, and g.

NMR data of HA-PLLA:

δ 4.59 (m, H-1), 4.50 (m, H-1'), 4.07 (m, H-2), 3.22 (m, H-2'), 3.94 (m, H-3), 3.60 (m, H-3'), 3.52 (m, H-4), 3.60 (m, H-4'), 3.37 (m, H-5), 3.52 (m, H-5'), 4.16 (m, H-6a), 3.92 (m, H-6b), 1.65 (m, H-a), 5.02 (m, H-b), 1.47 (d, J=7.2 Hz, H-c), 4.01 (m, H-d), 1.15 (S, H-e), 0.76 (t, J=7.0 Hz, H-f), 2.13 (s, H-g).

Example B-6

Synthesis of Hyaluronic Acid Copolymer Grafted with PCL Prepolymer ($HA_{20,000}$-g-100%-$PCL_{2,300}$ Copolymer)

1.15 g ($5 \times 10^{-4}$ mole) of mono-functional PCL (Mw=2300) was dissolved in 50 ml of NMP, and then 0.084 g of hexamethylene diisocyanate ($5 \times 10^{-4}$ mole) and 100 μl of di-n-butyltin dilaurate were added in sequence. The reaction temperature was 60° C. and the reaction time was 5 hours. After reaction, 0.2 g ($5 \times 10^{-4}$ mole) of quaternary ammonium salt of hyaluronic acid (Mw=20,000) was dissolved in 100 ml of DMSO and added to the above PCL solution. 100 μl of di-n-butyltin dilaurate was then added. The reaction temperature was 60° C. After 12 hours of reaction, DBA was added to stop the reaction, obtaining $HA_{20,000}$-g-100%-$PCL_{2,300}$ copolymer. The reaction mixture was dialyzed in saturated sodium chloride aqueous solution with a dialysis membrane (MWCO=3500), purified, exchanged from quaternary ammonium salt to sodium salt, and then freeze-dried.

Determination of Critical Micelle Concentration (CMC):

The $HA_{20,000}$-g-100%-$PCL_{2,300}$ copolymer was dissolved in 4 μM diphenyl hexatriene (DPH) solution at a concentration of 0.001%, 0.005%, 0.01%, 0.025%, 0.05%, 0.1%, 0.5%, and 1% respectively. Absorbance at 356 nm wavelength was measured with UV-VIS spectrometer. The CMC was 0.432 wt %.

Example B-7

Synthesis of Hyaluronic Acid Copolymer Grafted with PCL Prepolymer ($HA_{20,000}$-g-50%-$PCL_{2,300}$ Copolymer)

0.58 g ($2.5 \times 10^{-4}$ mole) of mono-functional PCL (Mw=2300) was dissolved in 50 ml of NMP, and then 0.042 g of hexamethylene diisocyanate ($2.5 \times 10^{-4}$ mole) and 100 μl of di-n-butyltin dilaurate were added in sequence. The reaction temperature was 60° C. and the reaction time was 5 hours. After reaction, 0.2 g ($5 \times 10^{-4}$ mole) of quaternary ammonium salt of hyaluronic acid (Mw=50,000) was dissolved in 100 ml of DMSO and added to the above PCL solution. 100 μl of di-n-butyltin dilaurate was then added. The reaction temperature was 60° C. After 12 hours of reaction, DBA was added to stop the reaction, obtaining $HA_{20,000}$-g-50%-$PCL_{2,300}$ copolymer. The reaction mixture was dialyzed in saturated sodium chloride aqueous solution with a dialysis membrane (MWCO=3500), purified, exchanged from quaternary ammonium salt to sodium salt, and then freeze-dried.

Determination of Critical Micelle Concentration (CMC):

The $HA_{20,000}$-g-50%-$PCL_{2,300}$ copolymer was dissolved in 4 μM diphenyl hexatriene (DPH) solution at a concentration of 0.001%, 0.005%, 0.01%, 0.025%, 0.05%, 0.1%, 0.5%, and 1% respectively. Absorbance at 356 nm wavelength was measured with UV-VIS spectrometer. The CMC was 0.255 wt %.

In conclusion, the present invention modifies native hyaluronic acid by introducing a short chain moiety or a prepolymer onto the —OH group via a urethane linkage. The hyaluronic acid derivative of the present invention has no cytotoxicity response. Moreover, the hyaluronic acid derivative grafted with a biodegradable hydrophobic prepolymer when dissolved in a hydrophilic medium forms micelles and has a low critical micelle concentration (CMC). Therefore, a pharmaceutically active or bioactive molecule can be entrapped in the hyaluronic acid derivative micelles to form a pharmaceutically active or bioactive composition with a stable controlled released effect.

The foregoing description of the preferred embodiments of this invention has been presented for purposes of illustration and description. Obvious modifications or variations are possible in light of the above teaching. The embodiments chosen and described provide an excellent illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A biodegradable hyaluronic acid derivative comprising at least one modified hyaluronic acid repeating unit represented by the formula (HA)-[O(C=O)NH-M]*p*, wherein HA is a unit including N-acetyl-D-glucosamine and D-glucuronic acid, M is a modifying moiety containing a biodegradable hydrophobic prepolymer, and p is an integer of 3 to 4, and wherein the biodegradable prepolymer is a biodegradable polyester-containing prepolymer.

2. The biodegradable hyaluronic acid derivative as claimed in claim 1, further comprising a native hyaluronic acid repeating unit including N-acetyl-D-glucosamine and D-glucuronic acid.

3. The biodegradable hyaluronic acid derivative as claimed in claim 1, which is a comb-like or brush-like shaped graft copolymer.

4. The biodegradable hyaluronic acid derivative as claimed in claim 1, wherein the biodegradable prepolymer is polycaprolactone (PCL), poly L-lactide (PLLA), polylactic acid (PLA), polyglycolic acid (PGA), poly-lactic-co-glycolic acid copolymer (PLGA copolymer), or polycaprolactone-polylactic acid copolymer (PCL-PLA copolymer).

5. The biodegradable hyaluronic acid derivative as claimed in claim 1, wherein the biodegradable prepolymer has a molecular weight of 500 to 200000.

6. A biodegradable polymeric micelle composition comprising:
a hydrophilic medium; and
a biodegradable hyaluronic acid derivative comprising a modified hyaluronic acid repeating unit represented by the formula (HA)-[O(C=O)NH-M]p, wherein HA is a unit including N-acetyl-D-glucosamine and D-glucuronic acid, M is a modifying moiety containing a biodegradable hydrophobic prepolymer, and p is an integer of 3 to 4, and wherein the biodegradable prepolymer is a biodegradable polyester-containing prepolymer,
wherein the biodegradable hyaluronic acid derivative forms micelles.

7. The biodegradable polymeric micelle composition as claimed in claim 6, wherein the biodegradable hyaluronic acid derivative has a concentration higher than a critical micelle concentration.

8. The biodegradable polymeric micelle composition as claimed in claim 7, wherein the biodegradable hyaluronic acid derivative is present in an amount of 0.005 to 0.5 wt % by the biodegradable polymeric micelle.

9. The biodegradable polymeric micelle composition as claimed in claim 8, wherein the biodegradable hyaluronic acid derivative is present in an amount of 0.005 to 0.3 wt % by the biodegradable polymeric micelle.

10. The biodegradable polymeric micelle composition as claimed in claim 6, wherein the biodegradable hyaluronic acid derivative is a comb-like shaped graft copolymer.

11. The biodegradable polymeric micelle composition as claimed in claim 6, wherein the biodegradable prepolymer is polycaprolactone (PCL), poly L-lactide (PLLA), polylactic acid (PLA), polyglycolic acid (PGA), poly-lactic-co-glycolic acid copolymer (PLGA copolymer), or polycaprolactone-polylactic acid copolymer (PCL-PLA copolymer).

12. The biodegradable polymeric micelle composition as claimed in claim 6, wherein the biodegradable prepolymer has a molecular weight of 500 to 200000.

13. The biodegradable polymeric micelle composition as claimed in claim 6, wherein the hydrophilic medium is water or an aqueous solution.

14. A pharmaceutical or bioactive composition comprising:
a hydrophilic medium;
a biodegradable hyaluronic acid derivative comprising a modified hyaluronic acid repeating unit represented by the formula (HA)-[O(C=O)NH-M]p, wherein HA is a unit including N-acetyl-D-glucosamine and D-glucuronic acid, M is a modifying moiety containing a biodegradable hydrophobic prepolymer, and p is an integer of 3 to 4, and wherein the biodegradable prepolymer is a biodegradable polyester-containing prepolymer; and a pharmaceutically active molecule or a bioactive molecule entrapped within micelles formed by the biodegradable hyaluronic acid derivative.

15. The pharmaceutical or bioactive composition as claimed in claim 14, wherein M contains a biodegradable hydrophobic prepolymer.

16. The pharmaceutical or bioactive composition as claimed in claim 15, wherein the biodegradable hydrophobic prepolymer is polycaprolactone (PCL), poly L-lactide (PLLA), polylactic acid (PLA), polyglycolic acid (PGA), poly-lactic-co-glycolic acid copolymer (PLGA copolymer), or polycaprolactone-polylactic acid copolymer (PCL-PLA copolymer).

17. The pharmaceutical or bioactive composition as claimed in claim 14, wherein the hydrophilic medium is water or an aqueous solution.

18. The pharmaceutical or bioactive composition as claimed in claim 14, wherein the biodegradable hyaluronic acid derivative is present in an amount of 0.005 to 0.5 wt % by the biodegradable polymeric micelle.

19. The pharmaceutical or bioactive composition as claimed in claim 18, wherein the biodegradable hyaluronic acid derivative is present in an amount of 0.005 to 0.3 wt % by the biodegradable polymeric micelle.

20. The pharmaceutical or bioactive composition as claimed in claim 14, wherein the pharmaceutically active or bioactive molecule is hydrophobic.

* * * * *